(12) United States Patent
Vadgama et al.

(10) Patent No.: US 6,200,459 B1
(45) Date of Patent: Mar. 13, 2001

(54) ANALYTICAL METHOD

(75) Inventors: Pankaj Madganlal Vadgama, Manchester; Ian McIntyre Christie, Stockport, both of (GB)

(73) Assignee: Sensalyse Holdings Limited, Manchester (GB)

( * ) Notice: Subject to any disclaimer, the term of this patent is extended or adjusted under 35 U.S.C. 154(b) by 0 days.

(21) Appl. No.: 09/230,832

(22) PCT Filed: Jul. 18, 1997

(86) PCT No.: PCT/GB97/01966

§ 371 Date: Sep. 27, 1999

§ 102(e) Date: Sep. 27, 1999

(87) PCT Pub. No.: WO98/04914

PCT Pub. Date: Feb. 5, 1998

(30) Foreign Application Priority Data

Jul. 31, 1996 (GB) .................................................. 9616088

(51) Int. Cl.$^7$ .................................................. G01N 27/26
(52) U.S. Cl. ........................ 205/787; 204/415; 422/82.06; 422/84
(58) Field of Search ........................ 204/415; 205/782.5, 205/783, 787; 422/82.06, 82.07, 84, 85

(56) References Cited

U.S. PATENT DOCUMENTS

| | | | | |
|---|---|---|---|---|
| 2,913,386 | * | 11/1959 | Clark | .................................... 204/415 |
| 3,700,579 | * | 10/1972 | Clifton et al. | ........................ 204/415 |
| 3,966,579 | * | 6/1976 | Chang et al. | ......................... 204/415 |
| 5,204,262 | * | 4/1993 | Meiering et al. | ....................... 422/98 |
| 5,429,726 | * | 7/1995 | Johnson et al. | .................... 205/782.5 |
| 5,470,755 | * | 11/1995 | Simon | ...................................... 422/85 |
| 5,624,538 | * | 4/1997 | Luft et al. | ............................. 204/432 |

FOREIGN PATENT DOCUMENTS

| | | | | |
|---|---|---|---|---|
| 0 368 474 | * | 5/1990 | (EP) | . |
| WO 94/02585 | * | 2/1994 | (WO) | . |

* cited by examiner

*Primary Examiner*—T. Tung
(74) *Attorney, Agent, or Firm*—Pillsbury Winthrop LLP

(57) ABSTRACT

A method and apparatus for detecting ethanol content of a sample wherein a membrane barrier comprising unplasticized PVC is interposed between the sample and detecting means.

11 Claims, No Drawings

ANALYTICAL METHOD

This invention relates to an analytical method and apparatus useful for the determination of ethanol in a fluid sample.

Many forms of analytical methods and apparatus have been proposed for the detection and measurement of various components in fluid samples, and commonly these rely on some form of membrane to control the extent to which the components present in a sample under examination can gain access to a detector (e.g. an electrode) at which they can then be detected and determined. Especially in electrolytic methods it is well known to make sensors using membranes to separate the media being analysed from the active electrode itself.

The main function of the membrane is to separate, as far as possible, those components which are desirable (i.e. can participate in the reactions at an electrode on which the desired determination depends) from interferents - i.e. compounds which may be present but are undesirable because they either interfere with the progress of the desired determination reactions or take part in reactions of their own which compete with those of the component sought and distort or overwhelm the signals which are to be measured. The forms of construction have much in common with each other, and mainly differ in the nature of the membrane or media within it or combined with it in some way.

Some forms of sensor devices rely on the components used to make the membrane, while others rely on the mode of fabrication of the membrane, selecting its physical properties (for example its porosity) or treatments given to it, as these factors can control its effectiveness and selectivity in use.

Other forms of sensors incorporate an enzyme, which converts one substrate compound or analyte into another which may then be more easily measured. Especially, it is known to use oxidase enzymes, which generate hydrogen peroxide—a substance which can be measured very conveniently and accurately by electrolytic methods, especially amperometric methods, and thereby provide a measure of the compound giving rise to the hydrogen peroxide. An example is European Patent No. 216577 which specifies an enzyme electrode sensor with a porous membrane barrier of a specified low (>5%) porosity.

Polyvinyl chloride (PVC) has been proposed as a material for the fabrication of membranes for sensors. It has been proposed for use in plasticised form, as described in European Patent No. 575412, where the plasticiser performs the necessary part of enabling the membrane to function and the PVC only serves to "carry" the plasticiser.

PVC in un-plasticised form has also been proposed for use as a membrane in European Patent No. 652942. In this, a membrane of un-plasticised PVC is shown to possess a selective permeability towards hydrogen peroxide and oxalate. The reason for this selective permeability of un-plasticised PVC itself is not understood, and the effect is surprising as it is not logically related to molecular size and/or charge. No indication or guidance has been given therein of any other species (if any) to which the PVC might be permeable, or why it should be permeable at all.

Such known sensor devices, utilising various membrane materials, have been aimed principally at the analysis of fluids for the presence of sugars, especially glucose, and other substances which may be oxidisable by enzyme action to form hydrogen peroxide. Examples of fluids described as being analysed by these prior devices include biological media for example blood and fruit.

We have now found that a membrane of un-plasticised PVC also has the surprising property of being permeable to ethanol. This is unexpected, as the known permeability of un-plasticised PVC (particularly as described in European Patent No. 652942) is so limited and unpredictable, and is very valuable because it can provide the basis for analytical methods and apparatus for detection and determination of ethanol by selective diffusion of this compound from a fluid sample. It is especially valuable because there is a great need for a convenient and efficient means which can be used for analysing and/or monitoring products in which alcohol (ethanol) is present and processes in which it is produced or present. Uses to which the discovery can be applied include, for example, (a) fermentation processes such as brewing and wine making, (b) the analysis of beer, wines, and other alcoholic liquids, drinks and the like, and (c) examination of process liquids, effluents and other media in which the presence of ethanol may require monitoring and/or control (because it may be either desirable or undesirable) for example for legal purposes.

Thus according to our invention we provide an improved method for detecting and/or determining ethanol in fluid samples which comprises interposing a membrane barrier composed of polyvinyl chloride (PVC) in un-plasticised form between the sample to be analysed and a detecting means providing an output representative of the content of said ethanol and allowing the ethanol to diffuse through the said barrier membrane and then measuring its presence at the detecting means.

Alternatively stated, our invention comprises a method for detecting and/or determining ethanol in fluid samples by allowing the ethanol to diffuse from a sample under examination through a barrier membrane to an ethanol-responsive detector means, characterised in that the barrier membrane is composed of polyvinyl chloride (PVC) in un-plasticised form.

According to our invention we also provide an improved sensor device for detecting ethanol present in fluid samples and providing an output representative of the ethanol content of said sample comprising comprising an ethanol-detecting means and a membrane barrier between the said ethanol-detecting means and the sample to be analysed, characterised in that the membrane barrier is composed of polyvinyl chloride (PVC) itself, in un-plasticised form.

For these purposes, the un-plasticised PVC membrane allows the passage of the ethanol through the PVC itself and not through any additive (e.g. a plasticiser) incorporated in it. Likewise, it does not operate by reliance on porosity (pores or open channels) through a PVC matrix, and therefore we describe the PVC as substantially non-porous. By the term "substantially non-porous" we mean that the membrane is made in a way which aims to avoid the presence of pores or open channels.

The PVC (polyvinyl chloride) may be any polymer of vinyl chloride, as for example those made and available commercially, but should be free from any added plasticiser (an ingredient which is often present in some commercial products intended for uses such as moulding). Such "un-plasticised" PVC polymers are readily obtainable in commerce, however, and it is necessary only for the quality and purity of any polymer to be checked—which can be done by reference to its specification or labelling, or (if necessary) by analysis. The molecular weight of the PVC is relatively non-critical, and most commercial grades will be satisfactory in use. A typical molecular weight is in the range 10,000 to 200,000, but others (and mixtures thereof) may be used if desired. Any commercially available PVC does not have a precise molecular weight but is a mixture of polymers of different molecular weights for which an "average" molecular weight may be quoted.

The un-plasticised polyvinyl chloride (PVC) may be made into membranes by any conventional method. Most conveniently, this can be done by solution-casting techniques, using solvents to dissolve the polymer and then forming the PVC film from the solution of PVC. This can be done very conveniently by spreading the solution on a plate or flat surface and allowing the solvent to evaporate. This spreading and evaporation can be adjusted appropriately, by simple trial, to allow the PVC to form a film of the desired thickness, degree of regularity or uniformity, and lack of if desired, for example casting, spin-coating, screen printing, or any combination of such techniques. A convenient solvent for the purpose is tetrahydrofuran (TEF), but other solvents or mixtures of solvents which are known to be able to dissolve PVC can be used if desired.

The thickness of the membranes can be of the order already used conventionally in the art, but may be varied as found most appropriate having regard for the particular mixed polymer composition being used and the conditions under which it is to be used. Thus, convenient thicknesses are those in the range 10 to 40 $\mu$m, though larger or smaller thicknesses can be used if desired.

The ethanol-detecting means may be any known in the art, and may be based on any property of ethanol which is detectable and measurable. For example, it may be based on an electrochemical, optical (e.g. spectrophotometric) or chemical detecting system, or any other known system— alone or in combination. Likewise, the detecting means may be such as to detect the ethanol directly (i.e. as ethanol itself) or indirectly, by detection and measurement of another product derived from it, for example by the action of an appropriate condition and/or reagent. Such indirect means may include an enzyme-based reaction system (for example using an oxidase or dehydrogenase enzyme), electrochemical systems (usually electrochemical oxidation), chemical mediation using reagents which can interact with the ethanol to form another product which may be determined more readily or conveniently, optical techniques (e.g. those based on the optical absorption characteristics of ethanol itself or some product derived from it, or combinations of one or more of these techniques.

Examples of chemical mediators include oxidising agents, for example dichromate, permanganate and like reagents, or mixtures thereof. Optical methods may include those in which the absorption characteristics measured may be in the visible part of the spectrum (e.g. as a colour visible to the eye) or in the ultraviolet or infrared parts of the spectrum. Such measurements may be made in known and conventional manner using conventional apparatus. Appropriate systems are known in the art, for example those used in devices for the detection of ethanol in a sample of a person's breath (the so-called "breathalyser"), in which the ethanol reacts with a chemical reagent to produce a change of colour, the extent of which can be quantified sufficiently to serve as an indication of the amount of ethanol in the sample.

Most conveniently, the detecting means is one of an electrochemical nature. Such a means may be based on potentiometric or amperometric measurement (or even a combination of these) of which amperometric measurement is usually found to be preferable.

The detecting means will usually comprise an electrode system and a liquid or gel phase electrolyte-containing medium. In most applications the electrolyte will be aqueous (i.e. aqueous or aqueous-based) but the use of non-aqueous electrolyte media (for example organic-based media) is not excluded.

Especially, in the devices and method of our invention, the sensor device comprises a detecting means in contact with an electrolyte medium and both associated with a membrane of polyvinyl chloride (PVC) itself, in un-plasticised form, which provides an interface for contact with a sample to be analysed and interposed between the active electrode (anode) of the cell used as detector. Alternative forms of construction may have (a) both the electrodes of the detecting means (cell) enclosed within the PVC membrane (so that both are separated from the sample) or (b) only the anode of the detecting means (cell) enclosed within the PVC membrane (so that the PVC membrane is between the electrodes and the cathode is not separated from the sample). Of these, the former is very convenient and compact, but the latter is more simple and is made practicable by the fact that PVC in un-plasticised form is less insulating in its properties, and $H^+$ ions can pass through it.

The governing factor is the fact that un-plasticised. PVC, in substantially non-porous form, has an excellent permeability to ethanol but is relatively impermeable to most (or almost all) of the other compounds commonly associated with ethanol in the fluids and other media in which it is to be determined.

As the permeability of un-plasticised PVC is not absolutely exclusive to ethanol alone (it is known to be permeable to oxalate, for example) and the mechanisms affecting its permeability are not understood, some other components present in a sample under examination may be able to pass through the PVC—even though in only a small amount. If this is found to occur they may not interfere with the ethanol detection but, if they do have a tendency to interfere, this can be remedied by appropriate selection or adjustment of the detection system and detecting means. Alternatively, correction for possible interferents can be achieved by appropriate processing of the data from the detecting means. If such adjustment is not convenient, then the possible interference may be remedied by addition of a reagent to the sample being examined or to the medium on the detector side of the PVC membrane to react with the potential interferents (e.g. chemically and/or enzymatically) to reduce or eliminate its effect. Other means known in the art for distinguishing different analytes (i.e. ethanol from other compounds) may be used if desired; for example, these can include one or more additional membranes which can impart an appropriate extra degree of selectivity of access of species to the ethanol-detector means and/or voltage modulation when electrochemical detector means are used.

The temperature of use of the sensor is most conveniently around ambient temperatures, e.g. in the range 5 to 40 degrees C.

The invention can also be applied to the detection and determination of compounds which cannot permeate through the PVC membrane. This can be done when the analyte sought can be made to generate ethanol in the sample by any appropriate agent or conditions. Thus, for example, an analyte which can generate ethanol by enzymic action can be determined indirectly by way of the detection and determination of the ethanol derived from it. For this, the appropriate reagent to bring about the generation of the ethanol may be added to the sample under examination and then, when the reagent has acted, the resulting ethanol can pass through the PVC membrane and be detected as such and the presence of the original analyte can be deduced from this.

The sensor device of our invention can have a single membrane or, if desired, multiple layers of membrane material. When multiple layers of membrane are used, these may be the same or different. The preference for the position to be occupied by the un-plasticised PVC membrane differs to some degree according to the particular use to which the sensor is being applied and what substrate compound is to be detected by the sensor (e.g. whether the ethanol is to be determined directly or indirectly.

When multiple membrane layers are used, any membrane layer or layers other than any comprised of un-plasticised PVC may be made of any of the wide variety of materials known in the art. Examples of these include dialysis membranes, and in general are preferably non-diffusion limiting membranes, at least to the extent that they do not limit diffusion and passage of desired species towards the detecting means. When un-plasticised PVC is used as in inner membrane (i.e. a layer which is not the outermost), then one or more outer layers may be used which are of material which protects the sensor assembly in a mechanical manner (e.g. from mechanical damage) or in a chemical or any other manner considered appropriate for the use to which it is to be applied. Thus for example, there may be used an outer layer comprising a polycarbonate (especially in a porous form).

The active electrode may be any of those known in the art, for example a metal electrode, but especially a platinum anode. This is most conveniently made in combination with a silver/silver chloride counter-electrode—as for example in the so-called Clark electrode, which comprises a platinum electrode surrounded, wholly or partially, by a silver/silver chloride ring.

The principal forms of construction of sensors for use in putting the present invention into practice are those well known in the art, with the difference being the membrane used and the compound sought for determination.

For these, the PVC membrane is assembled in conjunction with the detecting means so that the un-plasticised PVC membrane is interposed between the sample and the detecting means. The components (apart from the un-plasticised PVC membrane) are mainly the conventional ones, and the many variants known in the art may be used.

One practical and convenient form of construction is that in which the un-plasticised PVC membrane is put directly on to the detector means when this is an electrode, and relying on the external wetting of this combination with the sample to produce the electrolyte contact with the electrode as required to make the electrochemical operation of the detector means function.

For use as a membrane material, an un-plasticised PVC possesses unexpected advantages over many other materials, particularly over a plasticised PVC. Plasticised PVC can allow some partitioning and then passage of species through it, but this may favour higher molecular weight compounds—typically greater than 300 mw, i.e. much greater than ethanol (mw 46). In an un-plasticised PVC, the absence of plasticiser minimises such possible higher molecular weight partitioning ability and restricts diffusion pathways in the PVC. Consequently it is surprising that un-plasticised PVC is permeable to ethanol without having to rely on any pores formed in the membrane material to allow the passage of the ethanol.

As a result of its unusual properties, un-plasticised PVC can be used very conveniently for the determination of ethanol in alcoholic liquids containing high-molecular weight compounds, sugars, and many other components which would otherwise be expected to interfere with ethanol determination. This selectivity in favour of ethanol is a valuable property which is not easily found and is very useful in clinical and related analytical, diagnostic and monitoring work.

Our invention is especially convenient as it does not require application of such means as heat, vaporisation, a high difference in pressure across the membrane, or the like in order to make the ethanol pass through the un-plasticised PVC from a sample under examination.

Thus, our invention can be used for the analysis of a wide variety of fluid samples. Examples of these include alcoholic beverages (for example beer, wines and other fermentation products)—which may be in their final form or at intermediate stages in their manufacture. It is especially useful for the determination of the ethanol content of stocks of alcoholic liquids which are in storage or in bulk, and for which it may be difficult to take samples, as all our invention requires is to bring a small specimen of the liquid to be tested into contact with the sensor device as specified herein. The sensor can be very small and portable, and it can be used with the minimum of disturbance to the material being tested, for example stocks of alcoholic liquids being stored in casks or barrels in cellars. Obtaining a reliable measurement of ethanol content easily and accurately is of great importance for purposes of assessing and monitoring it for legal reasons, especially for determining the tax or duty payable as required by law.

An especial advantage of this invention is that the sensor device and method can be used very conveniently and effectively for the determination of ethanol over a very wide range of concentrations—from small fractions of a percent to 100% ethanol—without having to alter that part of the sensor device which contacts the specimen or sample under examination, but only having to adjust the processing of the data derived from that contact. The different concentrations of ethanol do not affect the performance of the PVC membrane, whereas many of the prior art membranes can be severely affected by concentration of analyte and are usable only for restricted ranges of analyte—which limits their usefulness in practice and in commercial conditions.

The present invention is also useful for the analysis of alcoholic liquors or beverages (for example beer, wines and other fermentation products), in their final form or at intermediate stages in their manufacture or storage, and also for the monitoring of a wide range of process, waste and effluent liquids. Thus, it can be used for examination of weakly alcoholic media (e.g. contents of brewing vessels and low-alcohol beverages) and strongly alcoholic liquids (e.g. distilled spirits and high-alcohol beverages), and also the waste or un-usable liquid portions of such media so that appropriate repayments of taxes can be obtained.

What is claimed is:

1. A method for detecting ethanol in fluid samples which comprises interposing a barrier membrane composed of polyvinyl chloride in unplasticized form between the sample to be analyzed and a detecting means providing an output representative of the content of said ethanol and allowing the ethanol to diffuse through the said barrier membrane and then measuring its presence at the detecting means.

2. A method for detecting ethanol in fluid samples by allowing the ethanol to diffuse from a sample under examination through a barrier membrane to an ethanol-responsive detecting means, wherein the barrier membrane is composed of polyvinyl chloride in unplasticized form.

3. A method as claimed in claim 1 or claim 2 wherein the polyvinyl chloride is substantially non-porous.

4. (Amended) A method as claimed in claims 1 or 2 wherein the molecular weight of the polyvinyl chloride is in the range 10,000 to 200,000.

5. A method as claimed in claims 1 or 2 wherein the unplasticized polyvinyl chloride may be made into membranes by solution casting techniques, using solvents to dissolve a polymer and then forming the polyvinyl chloride film from the solution of polyvinyl chloride.

6. A method as claimed in claims 1 or 2 wherein the thickness of the membrane is in the range 10 to 40 $\mu$m.

7. A method as claimed in claims 1 or 2 wherein the detecting means is one of an electrochemical nature.

8. A method as claimed in claims 1 or 2 wherein the detecting means comprises an electrode system and a liquid or gel phase electrolyte-containing medium.

9. A method as claimed in claims 1 or 2 wherein the temperature of the detecting means is around ambient temperatures.

10. A method as claimed in claims 1 or 2 wherein the barrier membrane comprises the unplasticized polyvinyl chloride membrane and one or more other membranes.

11. A method for using a sensor device for detecting ethanol present in fluid samples and providing an output representative of the ethanol content of said sample, said sensor device comprising an ethanol-detecting means and a membrane barrier between the said ethanol-detecting means and the sample to be analyzed, wherein the membrane barrier is composed of polyvinyl chloride in unplasticized form, said method comprising:

detecting ethanol in fluid samples by interposing the membrane barrier composed of polyvinyl chloride in unplasticized form between the sample to be analyzed and the detecting means providing an output representative of the content of said ethanol and allowing the ethanol to diffuse through the said membrane barrier and then measuring the presence of the ethanol at the detecting means.

* * * * *